United States Patent [19]

Cooper

[11] Patent Number: 4,904,671

[45] Date of Patent: Feb. 27, 1990

[54] DIHYDROPYRIDINE ANTIALLERGIC AND ANTIINFLAMMATORY AGENTS

[75] Inventor: Kelvin Cooper, Deal, United Kingdom

[73] Assignee: Pfizer Inc., New York, N.Y.

[21] Appl. No.: 311,317

[22] Filed: Feb. 15, 1989

[30] Foreign Application Priority Data

Feb. 25, 1988 [GB] United Kingdom ............... 8804439

[51] Int. Cl.$^4$ ..................... A61K 31/44; C07D 471/04
[52] U.S. Cl. ..................... 514/303; 514/333; 514/338; 514/340; 546/118; 546/256; 546/271; 546/276
[58] Field of Search ............... 546/118, 256, 271, 276; 514/303, 333, 338, 340

[56] References Cited

U.S. PATENT DOCUMENTS 4,788,205  11/1988  Cooper et al. ............... 546/256
4,801,598  1/1989   Cooper et al. ............... 546/271

Primary Examiner—Mary C. Lee
Assistant Examiner—Bernard I. Dentz
Attorney, Agent, or Firm—Peter C. Richardson; J. Trevor Lumb; James M. McManus

[57] ABSTRACT

4-Aryl-2,6-disubstituted-3,5-dicarbamyl-1,4-dihydropyridines and 4-Aryl-2,6-disubstituted-3-alkoxycarbonyl-5-carbamyl-1,4-dihydropyridines as antiallergy and antiinflammatory agents.

5 Claims, No Drawings

DIHYDROPYRIDINE ANTIALLERGIC AND ANTIINFLAMMATORY AGENTS

BACKGROUND OF THE INVENTION

This invention relates to certain dihydropyridines which are useful in the treatment of allergic and inflammatory conditions in humans and animals.

A number of 1,4-dihydropyridines have been previously described as antiischaemic and antihypertensive agents. These compounds are able to inhibit the movement of calcium into cells and are thus active in the treatment or prevention of a variety of cardiac conditions or as antihypertensive agents. (See for example EP-A-100189.) However the compounds of the present invention are potent and selective antagonists of platelet activating factor and as such they have clinical utility in a quite different area, namely in the treatment of allergic and inflammatory conditions such as asthma and arthritis respectively.

Platelet activating factor (PAF) (1-O-alkyl-2-acetyl-sn-glyceryl-3-phosphorylcholine) is an ether phospholipid whose structure was first elucidated in 1979. It is produced by, released from and interacts with many pro-inflammatory cells, platelets and the kidney. In addition to potent platelet aggregating activity, PAF exhibits a wide spectrum of biological activities elicited either directly or via the release of other powerful mediators such as thromboxane $A_2$ or the leukotrienes. In vitro, PAF stimulates the movement and aggregation of neutrophils and the release therefrom of tissue-damaging enzymes and oxygen radicals. These activities contribute to actions of PAF in vivo consistent with it playing a significant role in inflammatory and allergic responses. Thus, intradermal PAF has been shown to induce an inflammatory response, with associated pain, accumulation of inflammatory cells and increased vascular permeability, comparable with the allergic skin reaction following exposure to allergen. Similarly, both the acute bronchoconstriction and chronic inflammatory reactions elicited by allergens in asthma can be mimicked by intratracheal administration of PAF. Accordingly agents which antagonise the actions of PAF and consequently also prevent mediator release by PAF, will have clinical utility in the treatment of a variety of allergic inflammatory and hypersecretory conditions such as asthma, arthritis, rhinitis, bronchitis and urticaria.

In addition to the above, PAF has been implicated as being involved in a number of other medical conditions. Thus in circulatory shock, which is characterised by systemic hypotension, pulmonary hypertension and increased lung vascular permeability, the symptoms can be mimicked by infusion of PAF. This coupled with evidence showing that circulating PAF levels are increased by endotoxin infusion indicate that PAF is a prime mediator in certain forms of shock. Intravenous infusion of PAF at doses of 20–200 pmol $kg^{-1}$ $min^{-1}$ into rats results in the formation of extensive haemorrhagic erosions in the gastric mucosa and thus PAF is the most potent gastric ulcerogen yet described whose endogenous release may underlie or contribute to certain forms of gastric ulceration. Psoriasis is an inflammatory and proliferative disease characterised by skin lesions. PAF is pro-inflammatory and has been isolated from lesioned scale of psoriatic patients indicating PAF has a role in the disease of psoriasis. Also, increasing evidence supports a potential pathophysiological role for PAF in cardiovascular disease. Thus recent studies in angina patients show PAF is released during atrial pacing. Intracoronary injection of PAF in pigs induces a prolonged decrease in coronary flow and in guinea pig hearts it induces regional shunting and ischaemia. In addition, PAF has been shown to initiate thrombus formation in a mesenteric artery preparation, both when administered exogenously and when released endogenously. More recently PAF has been shown to play a role in brain ischaemia induced in animal models of stroke.

Thus the compounds of the invention, by virtue of their ability to antagonise the actions of PAF, will be of value in the treatment of the above conditions.

SUMMARY OF THE INVENTION

According to the present invention there are provided compounds of the formula (I):

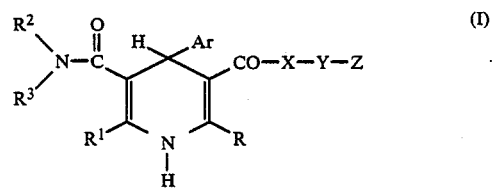

and their pharmaceutically acceptable salts; wherein Ar is chlorophenyl, dichlorophenyl, difluorophenyl, hydroxyphenyl or benzyloxyphenyl; R is alkyl of one to four carbon atoms, phenyl or fluorophenyl; $R^1$ is alkyl of one to four carbon atoms or phenyl; $R^2$ is alkyl of one to four carbon atoms or pyridyl; $R^3$ is hydrogen; X is O or NH; Y is $-(CH_2)_m-$ where m is 4 or 5 or

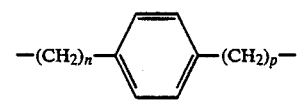

where n is 1 or 2 and p is 0 or 1; and Z is 2-methylimidazo[4,5-c]pyrid-1-yl, 1-methylimidazo[4,5-c]pyrid-2-yl, 3,5-dimethyl-1,2,4-triazol-4-yl or 2-methylbenzimidazol-1-yl.

Preferred are those compounds where Ar is 2-chlorophenyl, R is 4-fluorophenyl, $R^1$ is alkyl having one to four carbon atoms, $R^2$ is 2-pyridyl, X is O and Y is $-(CH_2)_m-$ where m is 4 or 5. Especially preferred within this group is the compound where $R^1$ is methyl, m is 4 and Z is 2-methylimidazo[4,5-c]pyrid-1-yl.

The compounds of the formula (I) containing at least one asymmetric centre will exist as one or more pairs of enantiomers, and such pairs of individual isomers may be separable by physical methods, e.g. by fractional crystallisation or chromatography of the parent compounds or of a suitable salt or derivatives thereof. The invention includes all the enantiomers whether separated or not.

The pharmaceutically acceptable acid addition salts of the compounds of the formula (I) are those formed from acids which form non-toxic acid addition salts, for example the hydrochloride, hydrobromide, sulphate or bisulphate, phosphate or acid phosphate, acetate, citrate, fumarate, gluconate, lactate, maleate, succinate, tartrate, methanesulphonate, benzenesulphonate and p-toluenesulphonate salts.

DETAILED DESCRIPTION OF THE INVENTION

The compounds of formula (I) may be obtained by the following processes in accordance with the invention.

In one particular process compounds of the present invention are prepared via the Hantzsch synthesis, according to the following reaction schemes:

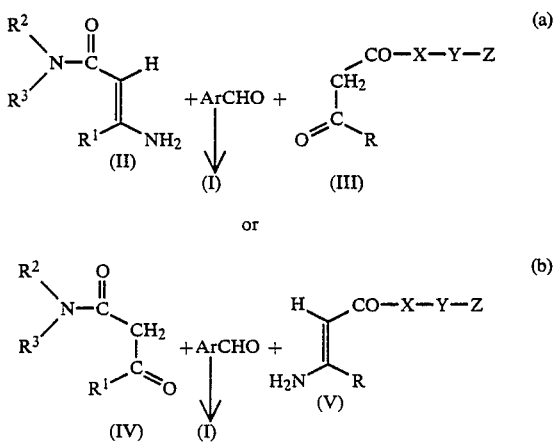

In the above, Ar, R, $R^1$, $R^2$, $R^3$, X, Y and Z are as defined for formula (I).

In a typical procedure, the keto-compound (III) or (IV) and aldehyde are heated under reflux in a suitable organic solvent, e.g. a $C_1$-$C_4$ alkanol such as ethanol, for about 15 minutes, and then the amino-compound (II) or (V) is added. Alternatively the amino-compound (II) or (V), the keto-compound (III) or (IV) and the aldehyde can be heated together in the solvent. Optionally a small amount of a lower alkanoic acid such as acetic acid is added to neutralise the solution. The resulting solution can then be heated at 60°–130° C., preferably under reflux, until the reaction is essentially complete, typically in 24 hours or less. The product of the formula (I) can then be isolated and purified by conventional procedures, for example by partition, recrystallisation or by chromatography.

The starting materials used in the above process are either known compounds or can be prepared conventionally, e.g. by the methods described in the following Preparations.

Certain compounds of the formula (I) are conveniently obtainable by simple chemical transformation reactions. For example, compounds of the formula (I) in which Ar is hydroxyphenyl are obtainable by the catalytic hydrogenation of the corresponding benzyloxy compounds, e.g. using hydrogen over palladium-on-charcoal in ethanol.

The activity of the compounds of the formula (I) and their salts is shown by their ability to inhibit the platelet aggregating activity of PAF in vitro. Testing is performed as follows:

Blood samples are taken from either rabbit or man into 0.1 vol disodium ethylenediamine tetraacetic acid buffer and the samples centrifuged for 15 minutes to obtain platelet rich plasma. The plasma is further centrifuged to give a platelet pellet which is washed with a buffer solution (4 mM $KH_2PO_4$, 6mM $Na_2HPO_4$, 100 mM NaCl, 0.1% glucose and 0.1% bovine serum albumin, pH 7.25) and finally resuspended in buffer solution to a concentration of $2 \times 10^8$ platelets/ml. A sample (0.5 ml) is pre-incubated for two minutes at 37° C. in a Paton aggregometer with stirring, either with vehicle alone, or with vehicle containing the particular compound under test. PAF is added at a sufficient concentration to give a maximum aggregating response in the absence of test compound ($10^{-8}$ to $10^{-9}$ molar), and the platelet aggregation is measured by following the increase in light transmission of the solution. The experiment is repeated in the presence of test compound at a range of concentrations and the concentration of compound required to reduce the response to 50% of its maximum value is recorded as the $IC_{50}$ value.

The activity of the compounds of formula (I) is also demonstrated in vivo by their ability to protect mice from the lethal effect of an injection of PAF. A mixture of PAF (50 μg/kg) and DL-propranolol (5 mg/kg) in 0.9% w/v sodium chloride is injected (0.2 ml) via a tail vein into mice. The compounds under test are either injected into the tail vein immediately prior to the PAF/propranolol injection or administered orally by gavage two hours earlier. The compounds are tested at several doses in groups of 5 mice and the dose which reduces mortality to 50% is recorded as the $PD_{50}$ value.

The compounds are also tested for their ability to reduce PAF-induced bronchoconstriction in anaesthetised guinea pigs. In this test airways resistance and dynamic lung compliance are calculated from recordings of airflow and transpleural pressure and calculation of tidal volume. The bronchoconstriction induced by PAF (100 ng/kg) is determined. One hour after the initial dose of PAF the compound under test is administered and the test repeated. The ability of the compound to reduce the bronchoconstrictor effect of PAF is recorded as a ratio.

For therapeutic use the compounds of the formula (I) will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For administration to man in the curative or prophylactic treatment of allergic bronchial conditions and arthritis, oral dosages of the compounds will generally be in the range of from 2–1000 mg daily for an average adult patient (70 kg.) Thus for a typical adult patient, individual tablets or capsules contain from 1 to 500 mg of active compound, in a suitable pharmaceutically acceptable vehicle or carrier. Dosages for intravenous administration would typically be within the range 1 to 10 mg per single dose as required. For the treatment of allergic and bronchial hyper-reactive conditions, inhalation via a nebuliser or aerosol may be the preferred route of drug administration. Dose levels by this route would be within the range 0.1 to 50 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

Thus in a further aspect the invention provides a pharmaceutical composition comprising a compound of the formula (I), or a pharmaceutically acceptable salt thereof, together with a pharmaceutically acceptable diluent or carrier.

The invention also includes a compound of the formula (I), or a pharmaceutically acceptable salt thereof, for use as a medicament, in particular for use in the treatment of allergic and inflammatory conditions in a human being.

The invention further includes the use of a compound of the formula (I), or of a pharmaceutically acceptable salt thereof, for the manufacture of a medicament for treating allergic and inflammatory conditions.

The following Examples, in which all temperatures are in °C., illustrate the invention. All the n.m.r. results were obtained in CDCl$_3$ at 300 MHz.

EXAMPLE 1

4-(2-Chlorophenyl)-2-(4-fluorophenyl)-3-[4-(2-methylimidazo[4,5-c]pyrid-1-yl)butoxycarbonyl]-6-methyl-5-(N-pyrid-2-ylcarbamoyl)-1,4-dihydropyridine A solution of N-(pyrid-2-yl)-3-aminocrotonamide (0.50 g, 2.8 mM), 2-chlorobenzaldehyde (0.39 g, 2.8 mM) and 4-(2-methylimidazo[4,5-c]pyrid-1-yl)butyl 3-(4-fluorophenyl)-3-oxopropionate (1.04 g, 2.8 mM—see Preparation 1) in absolute ethanol (15 cm$^3$) was heated at reflux, under nitrogen, for 5 hours. The cooled solution was evaporated to dryness and the residue purified by column chromatography on silica (Merck "Kieselgel 60"—Trade Mark) eluting with dichloromethane:methanol 97:3. The pure product-containing fractions were evaporated to dryness and the residual foam was re-dissolved in dichloromethane (2 cm$^3$). Addition of ether (25 cm$^3$) caused the product to crystallize out, yield 0.21 g, (12%), m.p. 129°–132°.

Analysis %: Found: C,66.37; H,5.03; N,12.75; C$_{36}$H$_{32}$ClFN$_6$O$_3$ requires: C,66.41; H,4.92; N,12.91.

N-(Pyrid-2-yl)-3-aminocrotonamide was obtained conventionally by the reaction of ammonia with the commercially available N-(acetoacetyl)-2-aminopyridine.

EXAMPLES 2–15

The following compounds were prepared by the method of Example 1 starting with the appropriate beta-ketoester (see Preparations 1–12), N-(pyrid-2-yl)-3-aminocrotonamide and the appropriately substituted benzaldehyde.

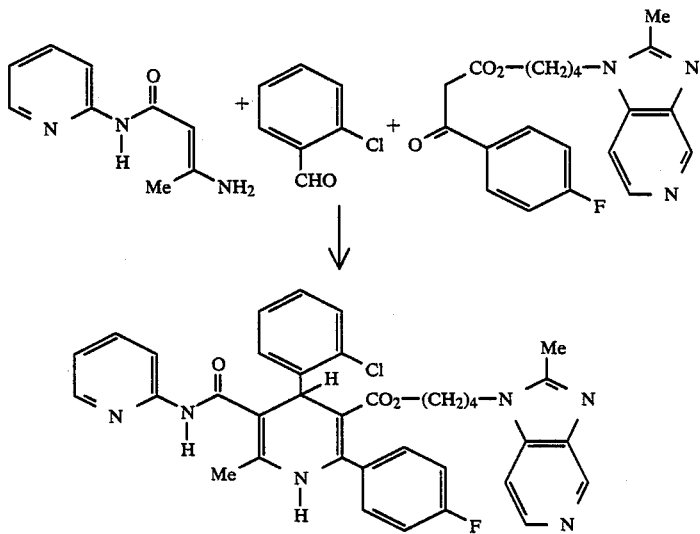

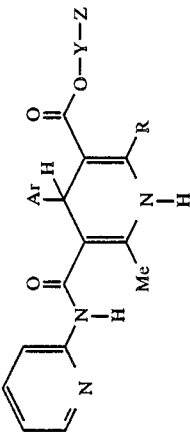
| Example No. | Ar | Y | Z | R | m.p. (°C.) | C | H | N |
|---|---|---|---|---|---|---|---|---|
| 2 | 2-Cl-C₆H₄ | —(CH₂)₄— | (Me-imidazo-pyridine) | C₆H₅ | 140–144 | 67.59 (67.34) | 5.42 5.30 | 12.88* 13.09 *Compound was isolated as a hemihydrate. |
| 3 | 2-Cl-C₆H₄ | —(CH₂)₂— | (Me-N-N-Me pyrazole) | C₆H₅ | 135–138 | 64.90 (64.92) | 5.40 5.66 | 13.46* 13.77 *Compound was isolated as ¼ hydrate. |
| 4 | 2-Cl-C₆H₄ | —(CH₂)₄— | (Me-N-N-Me pyrazole) | 4-F-C₆H₄ | 144–147 | 63.35 (63.51) | 5.31 5.29 | 13.29* 13.47 *Compound was isolated as a hemihydrate. |
| 5 | 2-Cl-C₆H₄ | —(CH₂)₅— | (Me-imidazopyridine-N-Me) | 4-F-C₆H₄ | 119–122 | 66.69 (66.82) | 5.17 5.12 | 13.02 12.64 |

-continued

| Example No. | Ar | Y | Z | R | m.p. (°C.) | Analysis % (Theoretical in brackets) C H N |
|---|---|---|---|---|---|---|
| 6 | 2-Cl-C6H4 | —(CH2)4— | Me-imidazo-pyridine | —Me | 201–208 | 63.56 5.67 13.81* (63.21) (5.65) (14.27) *Compound was isolated as a hydrate. |
| 7 | 2-Cl-C6H4 | —(CH2)4— | Me,Me-imidazole | —Me | 128–130 | 61.12 5.93 15.51* (60.81) (6.01) (15.20) *Compound was isolated as a hydrate. |
| 8 | 2,4-F2-C6H3 | —(CH2)4— | Me,Me-imidazole | Me | 85–90 | 61.09 6.04 14.88* (60.64) (5.82) (15.15) *Compound was isolated as a hydrate. |
| 9 | 2,4-Cl2-C6H3 | —(CH2)4— | Me,Me-imidazole | Me | 130–140 | 57.72 5.88 13.53* (57.69) (5.97) (13.46) *Compound was isolated as a hemi-etherate. |

-continued

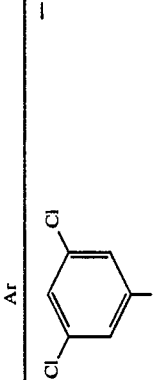

| Example No. | Ar | Y | Z | R | m.p. (°C.) | Analysis % (Theoretical in brackets) C | H | N |
|---|---|---|---|---|---|---|---|---|
| 10 | 3,5-dichlorophenyl | —(CH$_2$)$_4$— | Me–C=N–N=C–Me (N-) | Me | 125–135 | 56.38 (56.30) *Compound was isolated as a sesquihydrate. | 5.58 5.40 | 14.09* 13.80 |
| 11 | 2-benzyloxyphenyl | —(CH$_2$)$_4$— | Me–C=N–N=C–Me (N-) | Me | 172–180 | 67.84 (67.78) *Compound was isolated as a ¾ hydrate. | 6.45 6.42 | 13.63* 13.55 |
| 12 | 2-chlorophenyl | —(CH$_2$)$_2$—C$_6$H$_4$— | pyridyl-fused imidazole with Me | Me | 140–143 | 67.68 (67.91) | 5.11 5.01 | 13.48 13.58 |
| 13 | 2-chlorophenyl | —CH$_2$—C$_6$H$_4$—CH$_2$— | pyridyl-fused imidazole with Me | Me | 135–138 | 67.45 (67.41) *Compound was isolated as ¼ hydrate. | 5.08 5.09 | 13.53* 13.48 |

-continued

| Example No. | Ar | Y | Z | R | m.p. (°C.) | C | H | N |
|---|---|---|---|---|---|---|---|---|
| | | | | | | \multicolumn{3}{c}{Analysis % (Theoretical in brackets)} |
| 14 | 2-Cl-C6H4 | -CH2-C6H4- | 2-Me-imidazo[4,5-b]pyridine | Me | 150-152 | 67.44 (67.49) | 4.59 (4.80) | 14.00 (13.90) |
| 15 | 2-Cl-C6H4 | -(CH2)4- | 1-Me-2-Me-imidazo[4,5-b]pyridine | Me | 133-136 | 65.51 (65.21) | 5.42 (5.43) | 14.59 (14.72) |

EXAMPLE 16

5-(N-t-Butylcarbamoyl)-4-(2-chlorophenyl)-2,6-dimethyl-3-[4-(2-methylbenzididazol-1-yl)butoxycarbonyl]-1,4-dihydropyridine

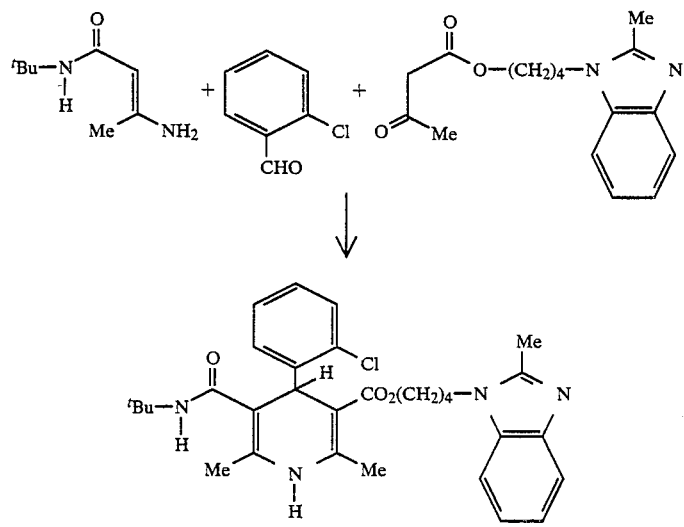

The title compound, m.p. 100°–106°, was prepared by the method of Example 1 using N-(t-butyl)-3-aminocrotonamide, 2-chlorobenzaldehyde and the above beta-ketoester (see Preparation 7).

Analysis %: Found: C,67.44; H,6.99; N,9.9; $C_{30}H_{37}ClN_4O_3$ requires: C,67.81; H,6.79; N,10.2.

N-(t-butyl)-3-aminocrotonamide was obtained conventionally by the reaction of ammonia with the commercially available N-(acetoacetyl)-t-butylamine.

EXAMPLE 17

2,6-Dimethyl-3-[4-(3,5-dimethyl-1,2,4-triazol-4-yl)butoxycarbonyl]-4-(2-hydroxyphenyl)-5-(N-pyrid-2-ylcarbamoyl)-1,4-dihydropyridine hydrate

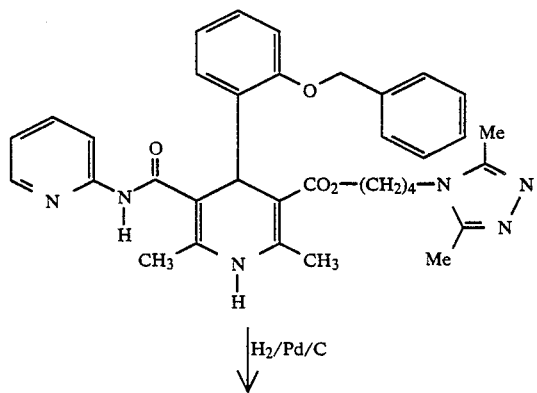

↓ H₂/Pd/C

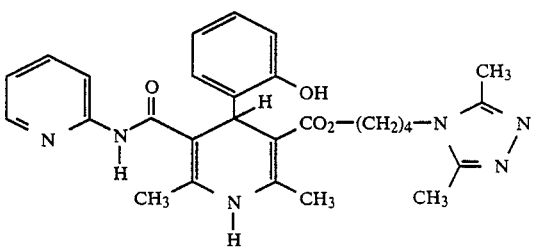

4-(2-Benzyloxyphenyl)-2,6-dimethyl-3-[4-(3,5-dimethyl-1,2,4-triazol-4yl)butoxycarbonyl]-5-(N-pyrid-2-ylcarbamoyl)-1,4-dihydropyridine (0.3 g—see Example 11) was dissolved in ethanol (10 ml) containing 10% palladium-on-charcoal and the mixture was hydrogenated at room temperature under pressure (30 p.s.i.=206.8 kPa) for 4 hours. The catalyst was filtered off and the filtrate evaporated under vacuum. The residue was then chromatographed on silica gel eluting with EtOAc containing 15% Et₂NH and the fractions containing the product were combined and evaporated to give the title compound, (0.12 g, 47%), m.p. 125°–135°.

Analysis %: Found: C,63.36; H,6.59; N,15.44; $C_{28}H_{32}N_6O_4.H_2O$ requires: C,62.91; H,6.41; N,15.72.

EXAMPLE 18

4-(2-Chlorophenyl)-3-[4-(2-methylimidazo[4,5-c]pyrid-1-yl)butoxycarbonyl]-2-methyl-6-phenyl-5-(N-pyrid-2-ylcarbamoyl)-1,4-dihydropyridine hemihydrate

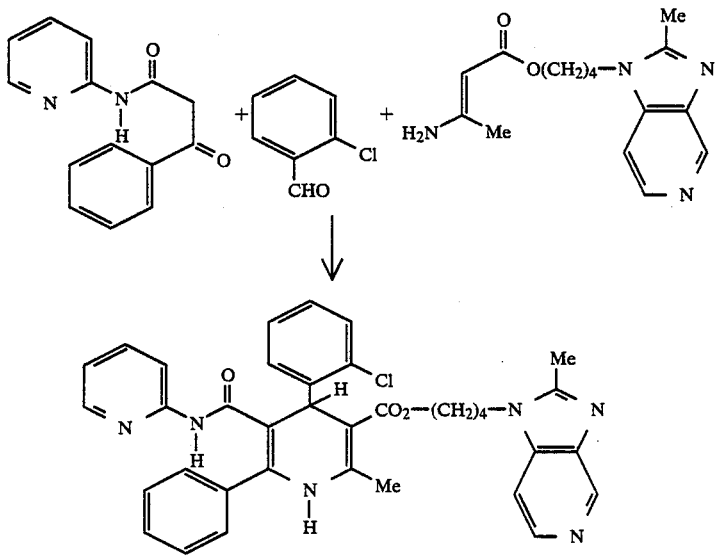

A solution of N-(pyrid-2-yl)-3-phenyl-3-oxopropionamide (0.84 g, 3.5 mM—see Preparation 15), 2-chlorobenzaldehyde (0.49 g, 3.5 mM) and 4-(2-methylimidazo[4,5-c]pyrid-1-yl)butyl 3-aminobut-2-enoate (1.01 g, 3.5 mM—see Preparation 13) in absolute ethanol (20 cm³) was heated at reflux, under nitrogen, for 16 hours. The cooled solution was evaporated to dryness and the residue purified by column chromatography on silica (Merck "Kieselgel 60"—Trade Mark) (2 passes) eluting primarily with ethyl acetate:diethylamine 97:3 and, secondly, dichloromethane: methanol 97:3. The product-containing fractions were evaporated to dryness, the residue re-dissolved in 2 cm³ dichloromethane, and the required solid precipitated by the addition of 25 cm³ ether, yield 0.35 g (16%), m.p. 124°–127°.

Analysis %: Found: C,67.19; H,5.29; N,13.09; $C_{36}H_{33}ClN_6O_3.\frac{1}{2}H_2O$ requires: C,67.34; H,5.3; N,13.09.

EXAMPLE 19

4-(2-Chlorophenyl)-2-(4-fluorophenyl)-3-[N-{4-(2-methylimidazo[4,5-c]pyrid-1-yl)butyl}carbamoyl]-6-methyl-5-(N-pyrid-2-ylcarbamoyl)-1,4-dihydropyridine hydrate

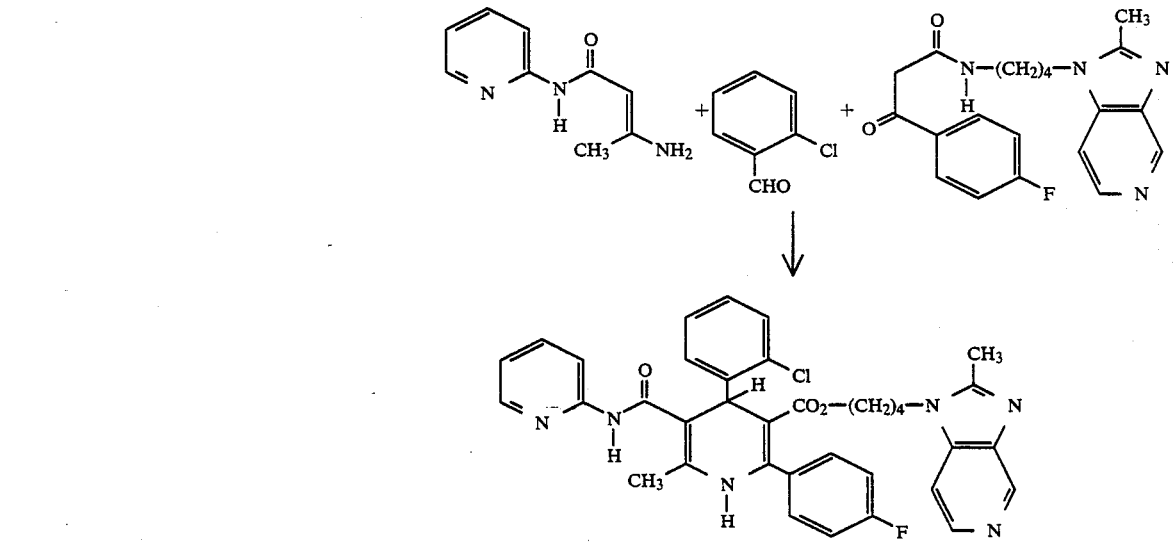

The title compound, m.p. 130°–133°, was prepared by the method of Example 1 using N-(pyrid-2-yl)-3-aminocrotonamide, 2-chlorobenzaldehyde and the above beta-ketoamide (see Preparation 14).

Analysis %: Found: C,64.65; H,5.27; N,14.69; $C_{36}H_{33}ClFN_7O_2.H_2O$ requires: C,64.72; H,5,24; N,14.68.

The following Preparations, in which all temperatures are in °C., illustrate the preparation of the novel starting materials used in the previous Examples:

PREPARATION 1

4-(2-Methylimidazo[4,5-c]pyrid-1-yl)butyl 3-(4-fluorophenyl)-3-oxo-propionate

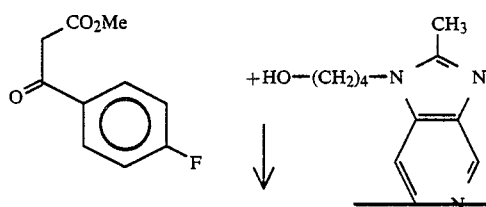

gave the title compound as a colourless oil, (1.05 g, 71%).

N.m.r. δ=1.75 (2H, m); 1.9 (2H, m); 2.65 (3H, s); 4 (2H, s); 4.15 (2H, t J=8); 4.25 (2H, t J=6); 7.15 (2H, m); 7.25 (1H, d J=6); 7.95 (2H, m); 8.4 (1H, d J=6); 9 (1H, s). M+=369.

PREPARATIONS 2-5

The following compounds were prepared by the method of Preparation 1 starting with the appropriate alcohol and benzoyl acetate:

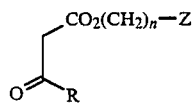

| Preparation No. | R | n | Z | N.m.r. δ = |
|---|---|---|---|---|
| 2 | phenyl | 4 | 2-Me-imidazo[4,5-c]pyridin-1-yl | 1.75(2H,m); 1.85(2H,m); 2.65(3H, s); 4.05(2H,s); 4.15(2H,t J=8); 4.25(2H,t,J=8); 7.25(1H,d J=6); 7.45(3H,m); 7.6(1H,t,J=6); 7.95(1H,d J=9); 8.4(1H,d,J=6); 9.0(1H,s). M+ =351. |
| 3 | phenyl | 4 | 3,5-dimethyl-1,2,4-triazol-4-yl | 1.7(4H,m); 2.4(6H,s); 3.75(2H, t,J=8); 4.05(2H,s); 4.25(2H,t J=8); 7.5(2H,m); 7.6(1H,t J=10); 7.95(2H,d J=10). M+ =315. |
| 4 | 4-fluorophenyl | 4 | 3,5-dimethyl-1,2,4-triazol-4-yl | 1.75(4H,m); 2.45(6H,s); 3.85(2H, t J=8); 4.05(2H,s); 4.25(2H,t J=8); 7.2(2H,ff J=10); 8.0(2H, m). M+ =333. |
| 5 | 4-fluorophenyl | 5 | 2-methyl-1-methylimidazo[4,5-c]pyridin-? | 1.55(2H,m); 1.75(2H,m); 1.95(2H, m); 2.9(2H,t J=8); 3.75(3H,s); 3.95(2H,s); 4.25(2H,t J=7); 7.15(2H,dd J=10); 7.25(1H,d J=6); 7.95(2H,m); 8.45(1H,d J=6); 9.05(1H,s). M+ =383. |

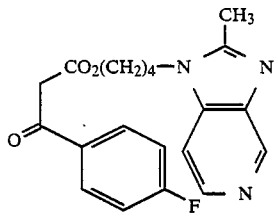

Methyl 4-fluorobenzoylacetate (0.78 g, 4 mM) and 4-(2-methylimidazo[4,5-c]pyrid-1-yl)butanol (0.82 g, 4 mM—see Preparation 16) were heated at reflux in toluene (100 cm³) allowing the toluene to reduce to about 20 cm³ over a period of 2 hours. The remaining toluene was removed in vacuo and the residue purified by column chromatography on silica (Merck "Kieselgel 60"—Trade Mark) eluting with dichloromethane:methanol 19:1. Evaporation of the appropriate fractions

PREPARATION 6

4-(2-Methylimidazo[4,5-c]pyrid-1-yl)butyl 3-oxobutanoate

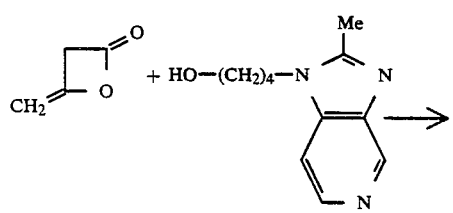

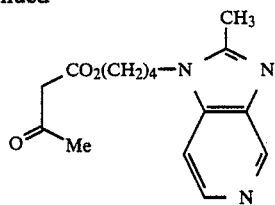

To a stirred solution of 2-methyl-1-(4-hydroxybutyl-)imidazo[4,5-c]pyridine (0.5 g) in acetone (10 ml) at room temperature was added, dropwise, freshly distilled diketene (0.2 g). The solution was stirred at room temperature for 2 hours and then evaporated to dryness. The residue was chromatographed on silica gel eluting with a methylene chloride-ethyl acetate mixture and the fractions containing the product were evaporated under vacuum to leave the title compound, (0.51 g).

N.m.r.δ=1.76 (2H, m); 1.95 (2H, m); 2.27 (3H, s); 2.67 (3H, s); 3.48 (2H, s); 4.2 (4H, m); 7.27 (1H, d, J=9Hz); 8.41 (1H, d, J=9Hz); 9 (1H, s).

PREPARATIONS 7–12

The following compounds were prepared by the method of Preparation 6 using the appropriate alcohol and diketene:

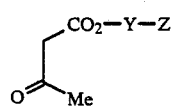

| Preparation No. | Y | Z | N.m.r. δ = |
|---|---|---|---|
| 7 | —(CH₂)₄— | 2-methylbenzimidazol-1-yl | |
| 8 | —(CH₂)₄— | 3,5-dimethyl-1,2,4-triazol-1-yl | 2.25(3H,s); 1.75(4H,m); 2.45(6H, s); 3.5(2H,s); 3.85(2H,t J=9); 4.2(2H,t J=9). |
| 9 | —(CH₂)₂—C₆H₄— | 2-methylimidazo[4,5-c]pyridin-1-yl | 2.25(3H,s); 2.55(3H,s); 3.1(2H, t J=7); 3.51(2H,s); 4.45(2H,t J=7); 7.1(1H,d J=5); 7.35(2H,d J=9); 7.5(2H,d J=9); 8.4(1H,d J=5); 9.05(1H,s). M⁺=337. |
| 10 | —CH₂—C₆H₄—CH₂— | 2-methylimidazo[4,5-c]pyridin-1-yl | 2.25(3H,s); 2.65(3H,s); 3.55(s, 2H); 5.2(s,2H); 5.35(2H,s); 7.05 (2H,d J=9); 7.2(1H,d J=6); 7.35(2H,d J=9); 8.4(1H,d J=6); 9.05(1H,s). M⁺=337. |
| 11 | —CH₂—C₆H₄— | 2-methylimidazo[4,5-c]pyridin-1-yl | 2.3(3H,s); 2.55(3H,s); 3.6(2H, s); 5.3(2H,s); 7.1(1H,d J=5); 7.4(2H,d J=9); 7.65(2H,d J=9); 8.4(1H,d J=5); 9.5(1H,s). M⁺=323. |

|              | 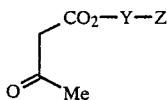 | | |
|---|---|---|---|
| Preparation No. | Y | Z | N.m.r. δ = |
| 12 | —(CH₂)₄— | (imidazo[4,5-c]pyridin-1-yl, N-Me) | 1.9(2H,m); 2.05(2H,m); 2.35(3H, s); 3.0(2H,t J=10), 3.55(2H,s); 3.80(3H,s); 4.25(2H,t J=10); 7.3(1H,d J=5); 8.45(1H,d J=5); 9.05(1H,s). M⁺=289. |

PREPARATION 13

4-(2-Methylimidazo[4,5-c]pyrid-1-yl)butyl 3-aminobut-2-enoate

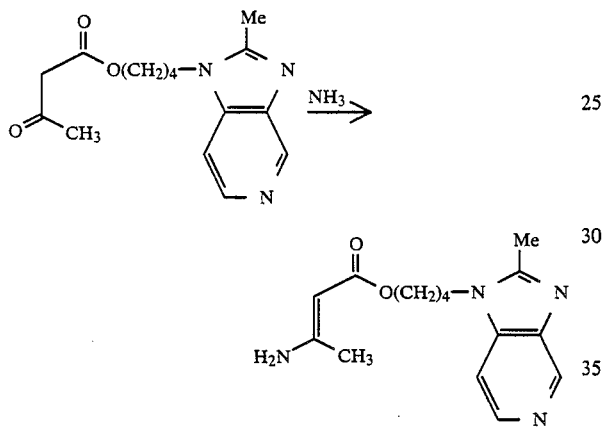

4-(2-Methylimidazo[4,5-c]pyrid-1-yl)butyl 3-oxobutanoate (1.52 g) (see Preparation 6) was dissolved in ethanol (50 ml) containing dry silica gel (2.5 g) and gaseous ammonia was then bubbled through the mixture for 20 minutes. The mixture was stirred at room temperature for a further 1½ hours and then filtered and evaporated to dryness leaving the crude title compound (1.54 g) which was used directly.

PREPARATION 14

N-[4-(2-Methylimidazo[4,5-c]pyrid-1-yl)butyl]-3-(4-fluorophenyl)-3-oxopropionamide

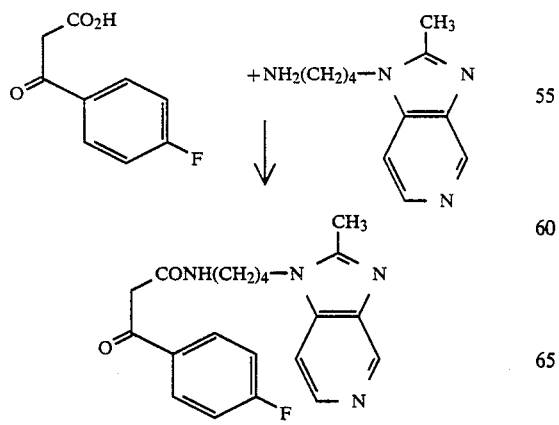

To an ice cold mixture of 3-(4-fluorophenyl)-3-oxoproprionic acid (prepared by standard saponification of the commercially available ester) (0.69 g), 1-hydroxybenzotriazole (0.56 g), and 4-(2-methylimidazo[4,5-c]pyrid-1-yl)butylamine (see Preparation 24) (0.71 g) in methylene chloride (20 cm³) was added 1-(3-dimethylaminopropyl)-3-ethylcarbodiimide hydrochloride (0.8 g) over 5 minutes. The mixture was stirred at 0° for 1 hour and then at room temperature for 30 minutes, poured into 5% sodium bicarbonate solution (50 ml) and extracted with methylene chloride (3×50 ml). The combined extracts were dried over Na₂SO₄, filtered and evaporated under vacuum. The residue was chromatographed on silica eluting with a methylene chloride/methanol mixture and the fractions containing the product were evaporated to give the title compound (0.82 g, 64%), which was used directly.

PREPARATION 15

N-(Pyrid-2-yl)-3-phenyl-3-oxopropionamide

The title compound was prepared as described by Barnish et. al. in *J. Org. Chem.*, 1968, 33, 2116.

PREPARATION 16

4-(2-Methylimidazo[4,5-c]pyrid-1-yl)butanol (a) 4-(4-Hydroxybutylamino)-3-nitropyridine

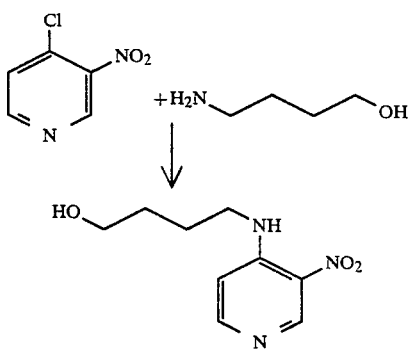

To a mixture of 4-chloro-3-nitropyridine (8 g) and NaHCO₃ (4.2 g) in ethanol (200 cm³) at room temperature was added over 3 minutes 4-aminobutanol (4.5 g). The mixture was stirred at room temperature for 1¼ hours and the solvent was then removed under vacuum. The residue was suspended in saturated aqueous NaHCO₃ solution (50 ml) and extracted with ethyl acetate (3×250 ml). The combined organic extracts were dried over Na₂SO₄, filtered and evaporated. The residue was then recrystallised from ethyl acetate to afford the title compound, (6.5 g, 62%), as yellow crystals, m.p. 80–82°.

(b) 3-Amino-4-(4-hydroxybutylamino)pyridine

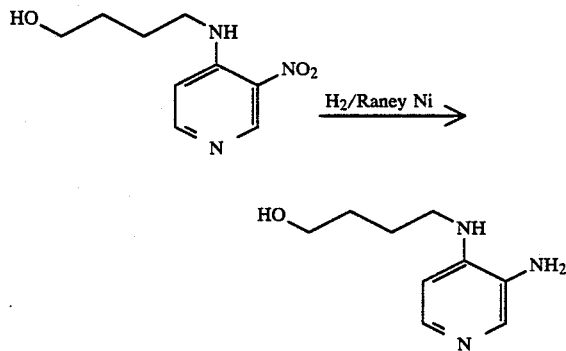

4-(4-Hyrdoxybutylamino)-3-nitropyridine (6 g) was dissolved in ethanol (60 cm³) containing Raney Ni catalyst (0.5 g) and then hydrogenated at room temperature for 3 hours under pressure (30 p.s.i.=206.8 kPa). The mixture was filtered under nitrogen and the filtrate was evaporated under vacuum to yield the crude product (5.5 g) which was used directly in the next step.

(c) 1-(4-Acetoxybutyl)-2-methylimidazo[4,5-c]pyridine

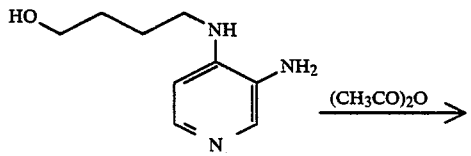

The crude amine from step (b) (13 g) was suspended in acetic anhydride (130 ml) and the mixture heated under reflux for 14 hours. The resulting solution was evaporated under vacuum and the residue dissolved in 1M hydrochloric acid and washed with methylene chloride (3×100 ml). The aqueous phase was then basified to pH 7.5 by the careful addition of solid NaHCO₃ and then extracted with methylene chloride (3×150 ml). The combined organic extracts were dried over Na₂SO₄, filtered, evaporated under vacuum and the residue was chromatographed on silica eluting with a mixture of methylene chloride and methanol. The fractions containing the product were evaporated to leave the title compound, (11.9 g), used directly (d) 4-(2-Methylimidazo[4,5-c]pyrid-1-yl)butanol

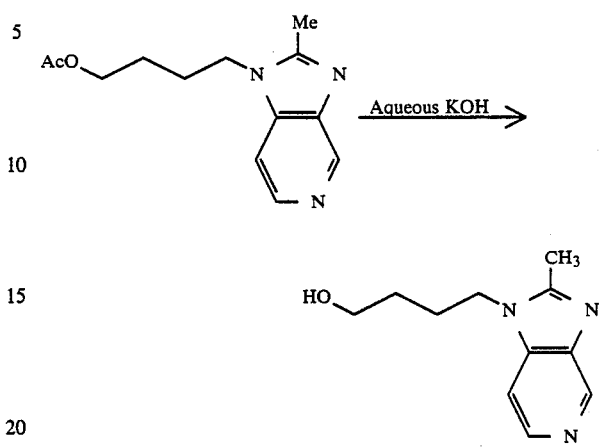

1-(4-Acetoxybutyl)-2-methylimidazo[4,5-c]pyridine (0.55 g) was dissolved in ethanol (10 ml) and 2M potassium hydroxide (2 ml) was added dropwise. The mixture was stirred at room temperature for 3 hours and then evaporated under vacuum. The residue was dissolved in 2M hydrochloric acid, washed with methylene chloride (2×20 ml), basified with solid NaHCO₃ to pH 7.5 and then extracted with methylene chloride (10×20 ml). The combined organic extracts were evaporated under vacuum to leave the desired product as a brown oil (0.5 g).

N.m.r.δ=1.58 (2H, m); 1.89 (2H, m); 2.57 (3H, s); 3.68 (2H, t, J=12); 4.37 (1H, brs); 7.2 (1H, d, J=9); 8.23 (1H, d, J=9); 8.87 (1H, s).

PREPARATION 17

4-(3,5-Dimethyl-1,2,4-triazol-4-yl)butanol

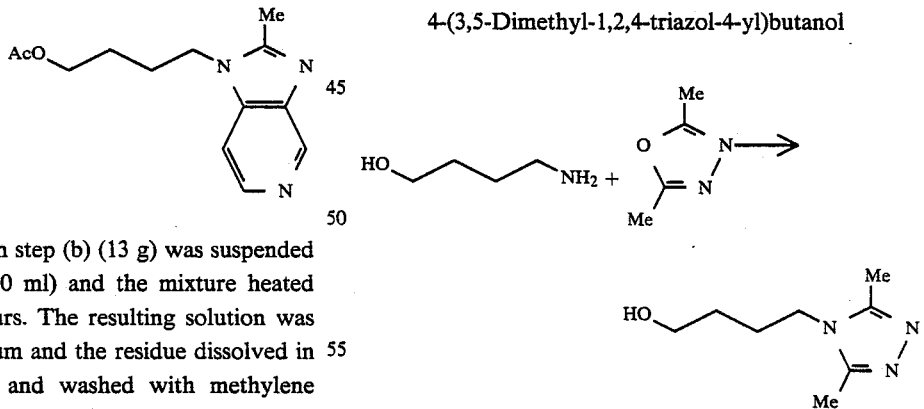

2,5-Dimethyl-1,3,4-oxadiazole (3.8 g), 4-aminobutanol (3.5 g) and N-methylpyrrolidone (10 ml) were heated at 150° for 18 hours. The mixture was evaporated under high vacuum and the residue chromatographed on silica eluting with a mixture of ethyl acetate and methanol. The fractions containing the product were evaporated under vacuum to leave the title compound, (5.1 g), which was used directly.

PREPARATION 18

5-(1-Methylimidazo[4,5-c]pyrid-2-yl)pentanol

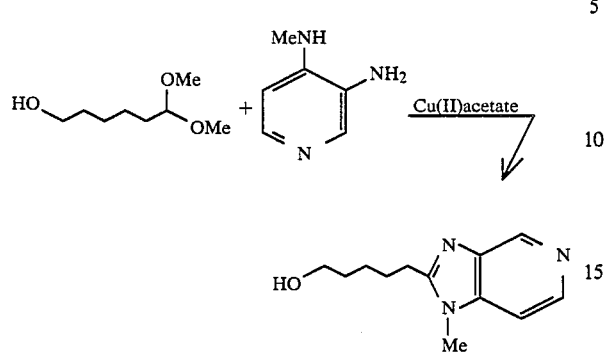

3-Amino-4-(methylamino) pyridine (1.23 g), 6,6-dimethoxyhexanol (1.62 g), copper (II) acetate monohydrate (4 g), ethanol (30 ml) and water (30 ml) were mixed and then heated at 150° in a sealed tube for 3 hours. To the cold reaction mixture was added concentrated aqueous ammonia (5 cm³) and the mixture was then filtered through "Hyflo" (Trade Mark), diluted with water (50 ml) and extracted with methylene chloride (3×200 ml). The combined organic extracts were dried over $Na_2SO_4$, filtered, and evaporated under vacuum. The residue was chromatographed on silica eluting with a mixture of methylene chloride and methanol. The fractions containing the product were evaporated to leave the title compound, (0.66 g).

N.m.r.δ=1.65 (4H, m); 2.00 (2H, m); 2.95 (2H, t J=10); 3.75 (2H, t J=10); 3.80 (3H, s); 7.25 (1H, m); 8.40 (1H, d J=5); 9.05 (1H, s).

PREPARATION 19

1-[4-(2-Hydroxyethyl)phenyl]-2-methylimidazo[4,5-c]pyridine (a) 4-[4-(2-Hydroxyethyl)phenylamino]-3-nitropyridine

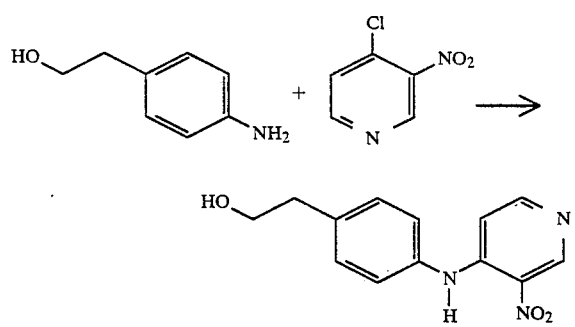

The title compound was prepared by the method of Preparation 16(a) using 4-(2-hydroxyethyl)phenylamine (5.5 g) giving the product as yellow crystals (6.5 g), m.p. 123°-125°.

Analysis %: Found: C,60.54; H,5.2; N,15.9; $C_{13}H_{13}N_3O_3$ requires: C,60.23; H,5.02; N,16.22.

(b)
3-Amino-4-[4-(2-hydroxyethyl)phenylamino]pyridine

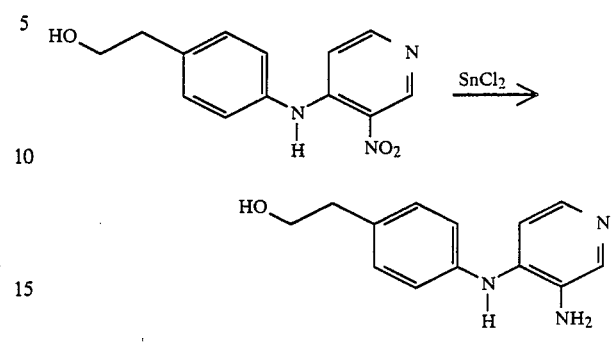

4-[4-(2-Hydroxyethyl)phenylamino]-3-nitropyridine (5.18 g) and stannous chloride dihydrate (22.56 g) were suspended in ethanol (100 ml) and heated at reflux for 45 minutes. The mixture was concentrated under vacuum, basified to pH8 with 2M sodium hydroxide solution and then extracted with ethyl acetate (3×200 ml). The combined organic extracts were dried over $Na_2SO_4$, filtered and evaporated under vacuum to give the crude product, (4.5 g), which was used directly in the next step.

(c)
1-[4-(2-Hydroxyethyl)phenyl]-2-methylimidazo[4,5-c]pyridine

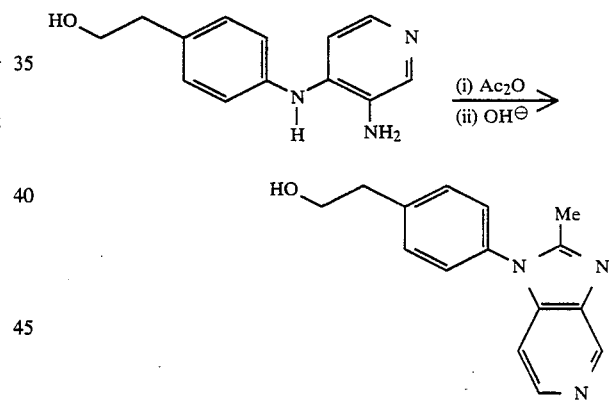

The title compound, m.p. 196°-8°, was prepared by the method of Preparations 16(c) and 16(d) using 3-amino-4-[4-(2-hydroxyethyl)phenylamino]pyridine as the starting material.

Analysis %: Found: C,71.99; H,6.16; N,16.5; $C_{15}H_{15}N_3O$ requires: C,71.15; H, 5.93;N,16.6.

PREPARATION 20

1-[4-(Hydroxymethyl)benzyl]-2-methylimidazo[4,5-c]pyridine (a) 4-(4-Ethoxycarbonylbenzylamino)-3-nitropyridine

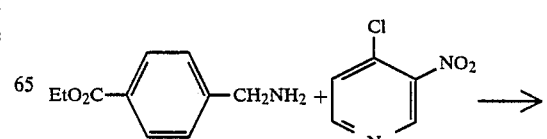

-continued

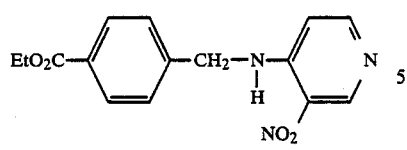

The title compound, m.p. 166°–8°, was prepared by the method of Preparation 16(a) using ethyl 4-aminomethylbenzoate and 4-chloro-3-nitropyridine as the starting materials.

Analysis %: Found: C,59.45; H,4.97; N,13.54; $C_{15}H_{15}N_3O_4$ requires: C,59.8; H,4.98; N,13.95.

(b) 3-Amino-4-(4-ethoxycarbonylbenzylamino)pyridine

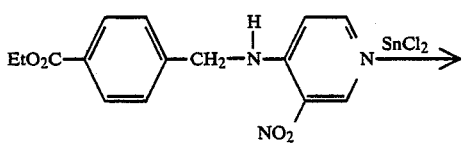

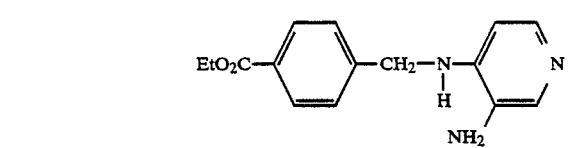

The title compound was prepared by the method of Preparation 19(b) using 4-(4-ethoxycarbonylbenzylamino)pyridine and stannous chloride dihydrate as the starting materials, and was used directly in the next step.

(c) 1-(4-Ethoxycarbonylbenzyl)-2-methylimidazo[4,5-c]pyridine

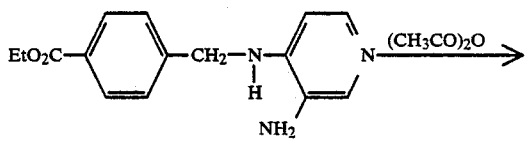

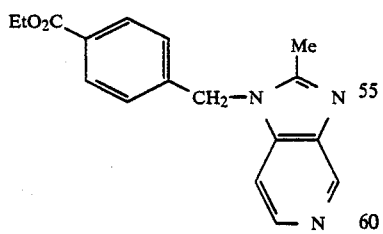

The title compound, m.p. 164°–6°, was prepared by the method of Preparation 16(c) using 3-amino-4-(4-ethoxycarbonylbenzylamino)pyridine and acetic anhydride as the starting materials.

Analysis %: Found: C,69.4; H,5.85; N,14.25; $C_{17}H_{17}N_3O_2$ requires: C,69.15; H,5.76; N,14.24.

(d) 1-[4-(Hydroxymethyl)benzyl]-2-methylimidazo[4,5-c]pyridine

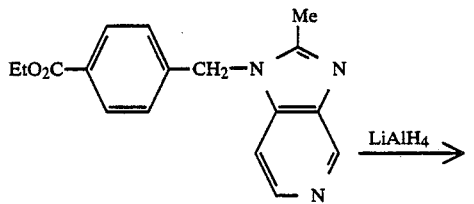

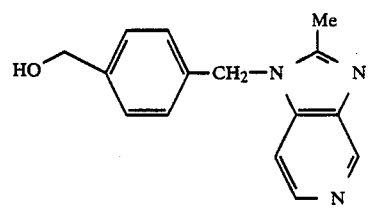

1-(4-Ethoxycarbonylbenzyl)-2-methylimidazo[4,5-c]pyridine (2.0 g) was suspended in tetrahydrofuran (50 ml) under $N_2$ and lithium aluminium hydride (0.16 g) was added portionwise over 5 minutes. The mixture was stirred at room temperature for 1 hour and then water was added cautiously, followed by saturated ammonium chloride solution. The mixture was extracted with ethyl acetate (3×50 ml) and the combined extracts were dried over $Na_2SO_4$, filtered and evaporated under vacuum. The residue was chromatographed on silica eluting with a mixture of methylene chloride and methanol and the fractions containing the product were evaporated to yield the title compound, (0.64 g).

N.m.r.δ=2.6 (3H, s); 3.15 (1H, OH broad); 4.75 (2H, s); 5.35 (2H, s); 7.05 (2H, d, J=9); 7.2 (1H, d J=5); 7.4 (2H, d J=9); 8.35 (1H, d J=5); 9.0 (1H,s).

PREPARATION 21

1-(4-Hydroxymethylphenyl)-2-methylimidazo[4,5-c]pyridine

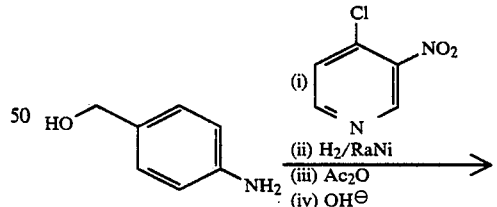

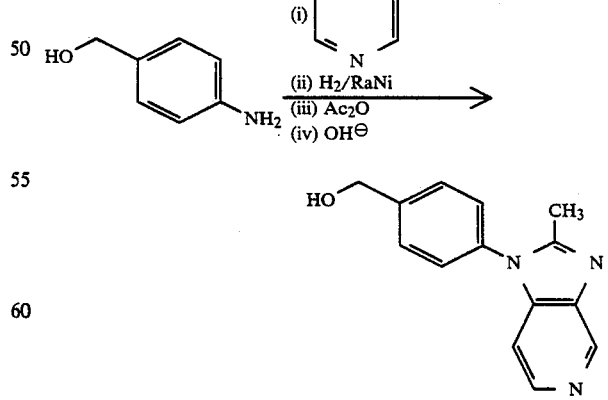

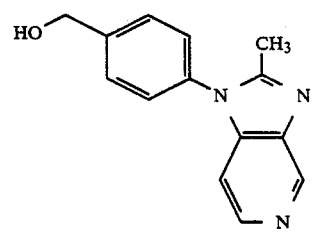

The title compound, m.p. 154°–6°, was prepared by the method outlined in Preparation 16 parts (a)–(d) using 4-aminobenzylalcohol and 4-chloro-3-nitropyridine as the starting materials.

Analysis %: Found: C,70.1; H,5.22; N,17.39; $C_{14}H_{13}N_3O$ requires: C,70.29; H,5.44; N,17.57.

PREPARATION 22

4-(1-Methylimidazo[4,5-c]pyrid-2-yl)butanol

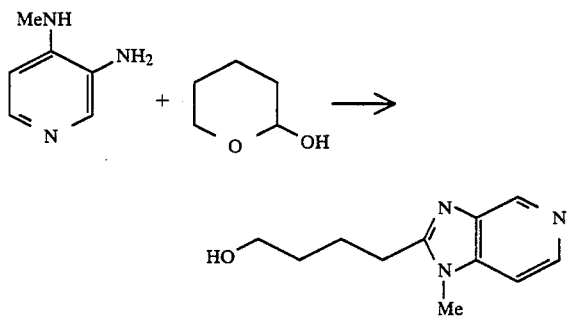

The title compound was prepared by the method of Preparation 18 using 2-hydroxytetrahydropyran and 3-amino-4-(methylamino)pyridine as the starting materials N.m.r.$\delta$=1.8 ((2H, m); 2.1 (2H, m); 3.0 (2H, t J=9); 3.75 (2H, t J=9); 3.80 (3H, s); 7.25 (1H, d J=5); 8.45 (1H, d J=5); 9.05 (1H, s).

PREPARATION 23

4-(2-Methylbenzimidazol-1-yl)butanol (a) 2-(4-Hydroxybutylamino)nitrobenzene

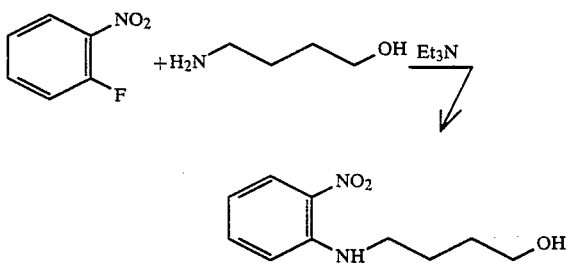

2-Fluoronitrobenzene (28 g), 4-aminobutanol (18 g) and triethylamine (29 ml) were dissolved in toluene (100 ml) and heated at 100° for 6 hours. The organic phase was washed with water (50 ml) and then extracted with concentrated hydrochloric acid (2×50 ml). The combined acid extracts were diluted with water (100 ml), neutralised with concentrated aqueous ammonia and extracted with methylene chloride (3×50 ml). The organic extracts were combined, dried over Na2SO4, filtered and evaporated to leave the title compound as a dark red oil (41 g) which was used directly in the next step.

(b) 2-(4-Hydroxybutylamino)phenylamine

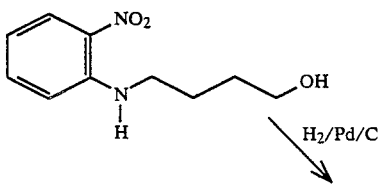

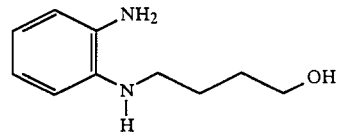

2-(4-Hydroxybutylamino)nitrobenzene (30 g) was dissolved in ethanol (200 ml) containing 10% palladium-on-carbon (1 g) and hydrogenated at room temperature for 3 hours under pressure (50 p.s.i.=344.7 kPa). The solution was filtered and evaporated under vacuum and the residue chromatographed on silica eluting with ethyl acetate. The fractions containing the product were evaporated under vacuum to give the title compound, (23.2 g), which was used directly in the next step.

(c) 4-(2-Methylbenzimidazol-1-yl)butanol

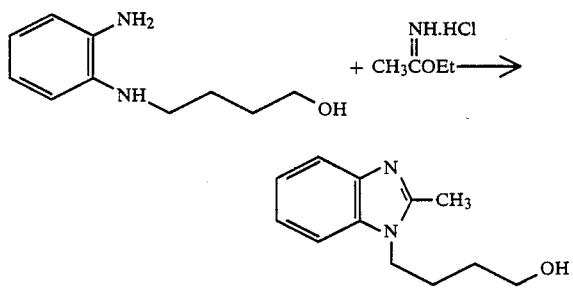

2-(4-Hydroxybutylamino)phenylamine (3.6 g) and ethyl acetimidate hydrochloride (3.7 g) was dissolved in ethanol (20 ml) and stirred at room temperature for 1½ hours. The mixture was evaporated under vacuum and the residue partitioned between ethyl acetate (30 ml) and water (20 ml). The organic phase was separated, dried over Na2SO4, filtered and evaporated to give the title compound as a brown oil (2.8 g).

N.m.r.$\delta$=1.66 (2H, m); 1.92 (2H, m); 2.6 (3H, s); 3.7 (2H, t J=9Hz); 4.15 (2H, t J=9Hz); 7.2–7.7 (4H, m).

PREPARATION 24

4-(2-Methylimidazo[4,5-c]pyrid-1-yl)butylamine (a) 4-(4-Aminobutylamino)-3-nitropyridine

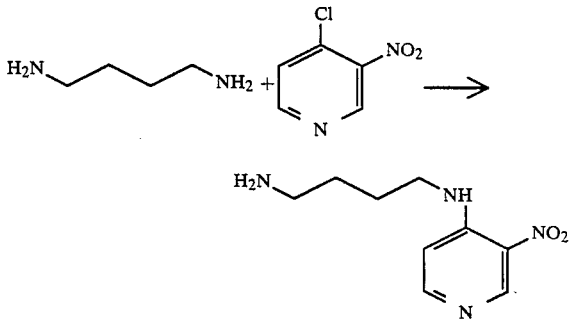

To a solution of 1,4-diaminobutane (8.8 g) in ethanol (100 ml) at room temperature was added a solution of 4-chloro-3-nitropyridine in ethanol (50 ml). The mixture was stirred at room temperature for 30 minutes, poured into ethyl acetate (400 ml), and then washed with water (3×150 ml). The aqueous phases were back-extracted with methylene chloride (3×120 ml) and all the organic phases were combined, dried over Na2SO4, filtered and evaporated under vacuum. The residue was chromatographed on silica eluting with a mixture of methylene chloride and methanol containing 1% ammonium hydroxide. The fractions containing the product were combined and evaporated under vacuum to give the title compound, (4.2 g), which was used directly in the next step.

(b) 3-Amino-4-(4-aminobutylamino)pyridine

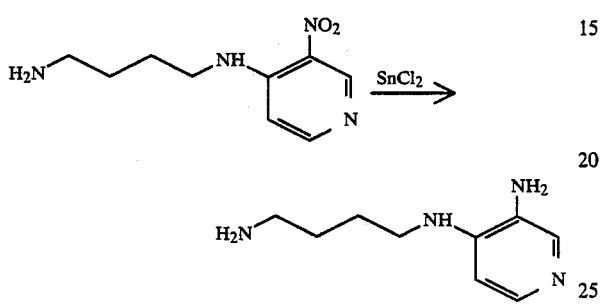

The title compound was prepared by the method of Preparation 19(b) using 4-(4-aminobutylamino)-3-nitropyridine and stannous chloride dihydrate as the starting materials.

(c) N-Acetyl-4-(2-methylimidazo[4,5-c]pyrid-1-yl)butylamine

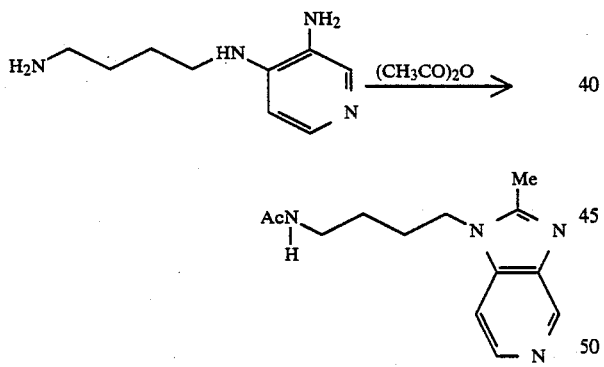

The title compound was prepared by the method of Preparation 16(c) using 3-amino-4-(4-aminobutylamino)pyridine and acetic anhydride as the starting materials.

(d) 4-(2-Methylimidazo[4,5-c]pyrid-1-yl)butylamine

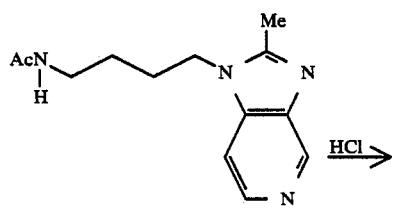

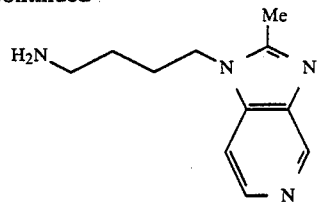

N-Acetyl-4-(2-methylimidazo[4,5-c]pyrid-1-yl)butylamine (1 g) was dissolved in 2M hydrochloric acid (100 ml) and heated at reflux for 8 hours. The solution was basified to pH8 with 2M sodium hydroxide solution and then extracted with methylene chloride using a continuous extractor. The organic extract was evaporated under vacuum to give the title product, (0.71 g).

N.m.r.δ=1.2 (2H, broad NH2); 1.55 (2H, m); 1.90 (2H, m); 2.70 (3H, s); 2.80 (2H, t J=10); 4.15 (2H, t J=10); 7.25 (1H, d, J =5); 8.40 (1H, d J=5); 9.00 (1H, s).

I claim:
1. A compound of the formula

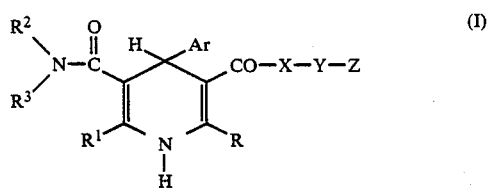

(I)

or a pharmaceutically acceptable salt thereof; wherein Ar is chlorophenyl, dichlorophenyl, difluororphenyl, hydroxyphenyl or benzyloxyphenyl; R is alkyl having one to four carbon atoms, phenyl or fluorophenyl; $R^1$ is alkyl having one to four carbon atoms or phenyl; $R^2$ is alkyl having one to four carbon atoms or pyridyl; $R^3$ is hydrogen; X is O or NH; Y is —(CH2)$_m$— where m is 4 or 5 or

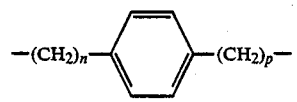

where n is 1 or 2 and p is 0 or 1; and Z is 2-methylimidazo[4,5-c]pyrid-1-yl, 1-methylimidazo[4,5-c]pyrid-2-yl, 2-methylbenzimidazol-1-yl or 3,5-dimethyl-1,2,4-triazol-4-yl.

2. A compound of claim 1, wherein Ar is 2-chlorophenyl, R is 4-fluorophenyl; $R^1$ is alkyl having one to four carbon atoms, $R^2$ is 2-pyridyl, X is O and Y is —(CH2)$_m$— where m is 4 or 5.

3. The compound of claim 2, wherein $R^1$ is methyl, m is 4 and Z is 2-methylimidazo[4,5-c]pyrid-1-yl.

4. A method for treating an inflammatory or allergic reaction in a mammal which comprises administering to said mammal an anti-inflammatory or anti-allergic effective amount of a compound according to claim 1.

5. A pharmaceutical composition in unit dosage form, useful for treating an inflammatory or allergic reaction in a mammal, comprising an inflammatory or allergic reaction treating amount of a compound according to claim 1 together with a pharmaceutically acceptable diluent or carrier.

* * * * *